(12) United States Patent
Westropp et al.

(10) Patent No.: US 11,666,609 B2
(45) Date of Patent: Jun. 6, 2023

(54) METHODS OF TREATING DOG URINARY TRACT INFECTIONS

(71) Applicants: The Regents of the University of California, Oakland, CA (US); Northwestern University, Evanston, IL (US)

(72) Inventors: JoEllen L. Westropp, Davis, CA (US); Anthony J. Schaeffer, Chicago, IL (US); David J. Klumpp, Chicago, IL (US)

(73) Assignees: The Regents of the University of California, Oakland, CA (US); Northwestern University, Evanston, IL (US)

( * ) Notice: Subject to any disclaimer, the term of this patent is extended or adjusted under 35 U.S.C. 154(b) by 0 days.

(21) Appl. No.: 16/769,962

(22) PCT Filed: Dec. 4, 2018

(86) PCT No.: PCT/US2018/063867
§ 371 (c)(1),
(2) Date: Jun. 4, 2020

(87) PCT Pub. No.: WO2019/113086
PCT Pub. Date: Jun. 13, 2019

(65) Prior Publication Data
US 2020/0397835 A1    Dec. 24, 2020

Related U.S. Application Data

(60) Provisional application No. 62/594,917, filed on Dec. 5, 2017.

(51) Int. Cl.
*A61K 35/741*    (2015.01)
*A61K 9/00*    (2006.01)

(52) U.S. Cl.
CPC .......... *A61K 35/741* (2013.01); *A61K 9/0034* (2013.01)

(58) Field of Classification Search
None
See application file for complete search history.

(56) References Cited

U.S. PATENT DOCUMENTS

| | | | |
|---|---|---|---|
| 8,877,178 B2 | 11/2014 | Boileau et al. | |
| 9,968,642 B2 | 5/2018 | Rudick et al. | |
| 2011/0171195 A1 | 7/2011 | Abraham et al. | |
| 2015/0320806 A1* | 11/2015 | Rudick | A61K 35/741 424/93.48 |

FOREIGN PATENT DOCUMENTS

WO    2012122472    9/2012

OTHER PUBLICATIONS

Westropp et al (Abstract NU21, J. Vet. Intern Med., vol. 29, pp. 1122 and 1216, 2015).*
Segev et al. (2018) "Evaluation of the Live Biotherapeutic Product, Asymptomatic Bacteriuria *Escherichia coli* 2-12, in Healthy Dogs and Dogs with Clinical Recurrent UTI" Journal of Veterinary Internal Medicine, 32(1):1267-273.
Thompson et al. (2011) "Experimental colonization of the canine urinary tract with the asymptomatic bacteriuria *Escherichia coli* strain 83972" Veterinary Microbiology, 147(1-2):205-208.
Darouiche at al. (2001) "Pilot Trial of Bacterial Interference for Preventing Urinary Tract Infection" Urology, 58(3):339-344.

* cited by examiner

*Primary Examiner* — Brian Gangle
(74) *Attorney, Agent, or Firm* — Brian E. Davy; Bozicevic, Field & Francis LLP (57) ABSTRACT

Provided are methods for treating acute and recurring urinary tract infections in dogs.

9 Claims, 2 Drawing Sheets

METHODS OF TREATING DOG URINARY TRACT INFECTIONS

CROSS-REFERENCE TO RELATED APPLICATIONS

This application claims the benefit of U.S. Provisional Patent Application No. 62/594,917 filed Dec. 5, 2017, which application is incorporated herein by reference in its entirety.

BACKGROUND

Uncomplicated bacterial urinary tract infections (UTI), also known as sporadic bacterial cystitis, is common and occurs in approximately 14% of dogs evaluated for medical care (1). Simple, uncomplicated UTI in small animals generally occur in otherwise healthy animals with no evidence of underlying disease and resolve with proper antimicrobial therapy (2). In human beings, bacterial UTI is the second most common infectious disease (3). Recurrent UTI also occurs in dogs and human beings and occasionally are associated with an underlying comorbidity (4). At a referral hospital, 0.3% of the dog population was diagnosed with recurrent infections, i.e. reinfections, persistent, or relapsing infections over a 26-year period (5). Antimicrobials are prescribed for clinical UTI and antimicrobial resistance has been an emerging problem in both dogs and humans (6, 7-8), and other treatment modalities are being investigated.

Recently, researchers have investigated administration of asymptomatic bacteriuria (ASB) 83972 into atonic bladders of human patients with chronic bacteriuria secondary to spinal cord injuries as an alternative therapy. Instillation of ASB *E. coli* 83972 improved the patients' quality of life (9), and none of the patients in this clinical trial developed signs of bacteremia or sepsis. Moreover, in patients where long-term bladder colonization by the bacteria was achieved, no symptoms of UTI developed. No adverse impact of ASB *E. coli* 83792 on renal function were reported (10). The mechanisms by which ASB *E. coli* provides protection for recurrent UTI are not fully understood. Without being bound to theory, the mechanisms might be due to immunomodulation or bacterial interference, whereby the ASB strains colonize the bladder and prevent colonization with uropathogenic *E. coli* (UPEC) strains that cause inflammation and result in lower urinary tract signs.

ASB *E. coli* can significantly reduce bacteriuria in murine UTI models of acute cystitis (11). Various ASB *E. coli* strains also have anti-infective and visceral analgesic activity when evaluated in these mouse models using UPEC strain NU14 to induce clinical cystitis (11). Moreover, the strain ASB *E. coli* 2-12, provided the greatest analgesic activity against cystitis pain and was superior to ciprofloxacin when evaluating tactile allodynia of the pelvic region in mice using mechanical stimulation. The superior analgesic properties of ASB *E. coli* 2-12 suggest this strain might be a viable option for management of isolated acute and perhaps recurrent UTI in human beings and dogs. While safety trials evaluating the effects of intravesicular administration of ASB *E. coli* 83972 were performed in two different dog pilot studies (12,13), neither the safety nor efficacy of ASB *E. coli* 2-12 administration has been evaluated in dogs or humans with acute, or recurrent UTI.

SUMMARY

In one aspect, provided are methods of reducing, mitigating, ameliorating, inhibiting or eliminating one or more clinical signs (e.g., symptoms) associated with an urinary tract infection (UTI) in a dog. In some embodiments, the methods comprise administering via one or more intravesicular instillations into the bladder of the dog a sufficient number of asymptomatic bacteriuria (ASB) *Escherichia coli* 2-12 colony forming units (CFUs) (e.g., viable cells), wherein ASB *Escherichia coli* 2-12 is deposited with the American Type Culture Collection under Accession Number PTA-124177. In some embodiments, the dog is exhibiting clinical signs of an acute or recurring UTI. In another aspect, provided are methods of preventing, delaying or avoiding a recurrent UTI in a dog having a history of recurring UTIs, comprising administering via one or more intravesicular instillations into the bladder of the dog a sufficient number of asymptomatic bacteriuria (ASB) *Escherichia coli* 2-12 CFUs, wherein ASB *Escherichia coli* 2-12 is deposited with the American Type Culture Collection under Accession Number PTA-124177. In some embodiments, the dog is exhibiting one or more clinical signs (e.g., symptoms) of UTI, e.g., detectable pathogenic bacteria, blood, cloudiness or opacity or foul smell in urine, and/or behavioral changes including without limitation demonstrably painful urination, frequent urination of small volumes, urinary incontinence, licking of penis/vulvar area. In some embodiments, the dog is asymptomatic (e.g., not exhibiting one or more clinical signs of UTI), and the intravesicular instillation comprises a prophylaxis to deter a recurring UTI. In some embodiments, the ASB *Escherichia coli* 2-12 CFUs transiently colonize in the dog's bladder, for example, the ASB *Escherichia coli* 2-12 CFUs may transiently colonize in the dog's bladder for at least about 8 days, e.g., at least about 10, 15, 20, 30, 35, 40, 45, 50, 55, 60 days, or more. In some embodiments, about $10^6$-$10^{16}$ colony-forming units (CFU), e.g., about $10^{10}$-$10^{11}$ CFU, e.g., about $10^6$, $10^7$, $10^8$, $10^9$, $10^{10}$, $10^{11}$, $10^{12}$, $10^{13}$, $10^{14}$, $10^{15}$, $10^{16}$ CFUs of ASB *E. coli* 2-12 are instilled into the bladder. In some embodiments, the methods comprise administering ASB *Escherichia coli* 2-12 via two or more intravesicular instillations, e.g., 2, 3, 4, 5, 6, 7, 8, or more instillations, into the bladder of the dog. In some embodiments, the two or more intravesicular instillations into the bladder are administered about every 2 to 14 days, e.g., about every 2 to 7 days, e.g., about every 2, 3, 4, 5, 6, 7, 8, 9, 10, 11, 12, 13, 14 days. In some embodiments, the dog has undergone serial catheterizations. In some embodiments, an indwelling catheter is not used. In some embodiments, an indwelling catheter is used. In some embodiments, the dog is a female. In some embodiments, the dog has one or more clinical signs of pollakiuria, hematuria and/or stranguria. In some embodiments, the dog does not have one or more clinical signs of pollakiuria, hematuria and/or stranguria. In some embodiments, the dog does not have and is not suspected of having cystic neoplasia, cystic calculi, an uncorrected ectopic ureter. In some embodiments, the dog has not been administered an antibiotic within 3 days prior to instillation. In some embodiments, the dog has no detectable antibiotic in the blood. In some embodiments, the dog has not received Cefovecin (Convenia®), or has no detectable Cefovecin (Convenia®) in the blood. In some embodiments, the one or more intravesicular instillations into the bladder of the dog reduces or clears the bacterial infection of the urinary tract. In some embodiments, the dog does not experience a recurrent infection, e.g., within 1, 2, 3, 4, 5, 6 months of receiving the first instillation. In some embodiments, the one or more intravesicular instillations into the bladder of the dog achieves microbiological cure. In some embodiments, the one or more intravesicular instillations into the bladder of the dog achieves clinical cure.

Definitions

As used herein, the terms "dog," "canine" and "*Canis lupus familiaris*" are used interchangeably.

As used herein, the terms "treating" and "treatment" refer to delaying the onset of, retarding or reversing the progress of, reducing the severity of, or alleviating or preventing either the disease or condition to which the term applies (i.e., urinary tract infections (UTI) or sporadic bacterial cystitis), or one or more clinical signs (e.g., symptoms) of such disease or condition.

The term "mitigating" refers to reduction or elimination of one or more clinical signs (e.g., symptoms) of that pathology or disease, and/or a reduction in the rate or delay of onset or severity of one or more clinical signs (e.g., symptoms) of that pathology or disease, and/or the prevention of that pathology or disease.

The term "effective amount" or "therapeutically effective amount" refers to the amount of an active agent sufficient to induce a desired biological result (e.g., prevention, delay, reduction or inhibition of one or more clinical signs (e.g., symptoms) of an UTI). That result may be alleviation of the signs, symptoms, or causes of a disease, or any other desired alteration of a biological system. The term "therapeutically effective amount" is used herein to denote any amount of the formulation which causes a substantial improvement in a disease condition when administered once or multiple times over a period of time. The amount will vary with the condition being treated, the stage of advancement of the condition, and the type and concentration of formulation applied. Appropriate amounts in any given instance will be readily apparent to those skilled in the art or capable of determination by routine experimentation.

A "therapeutic effect," as that term is used herein, encompasses a therapeutic benefit and/or a prophylactic benefit as described above. A "prophylactic effect" includes delaying or eliminating the appearance of a disease or condition, delaying or eliminating the onset of signs or symptoms of a disease or condition, slowing, halting, or reversing the progression of a disease or condition, or any combination thereof.

The terms "inhibiting," "reducing," "decreasing" with respect to an UTI refers to inhibiting one or more clinical signs (e.g., symptoms) of the UTI in a subject by a measurable amount using any method known in the art (e.g., pathologic bacteria in a urine sample, blood in urine sample, cloudy or malodorous urine), changes in dog behavior (e.g., difficulty or ease in urinating, frequent urination, urinary incontinence, urination when bladder is touched or pressed). The one or more clinical signs (e.g., symptoms) of the UTI are inhibited, reduced or decreased if the measurable parameter of the one or more clinical signs (e.g., symptoms) is at least about 10%, 20%, 30%, 50%, 80%, or 100% reduced in comparison to the measurable parameter of the one or more clinical signs (e.g., symptoms) prior to the one or more instillations of asymptomatic bacteriuria (ASB) *E. coli* 2-12 to the bladder. In some embodiments, the measurable parameter of the one or more clinical signs (e.g., symptoms) is inhibited, reduced or decreased by at least about 1-fold, 2-fold, 3-fold, 4-fold, or more in comparison to the measurable parameter of the one or more clinical signs (e.g., symptoms) prior to administration of the one or more instillations of asymptomatic bacteriuria (ASB) *E. coli* 2-12 to the bladder.

DETAILED DESCRIPTION

1. Introduction

Provided are methods of treating acute or recurrent urinary tract infections (UTIs) in a dog. In various embodiments, the methods entail intravesicular administration (also known as "intravesical" administration) to the bladder of a dog suffering from UTI a sufficient amount or number of asymptomatic bacteriuria (ASB) *E. coli* 2-12 to alleviate pelvic pain and/or to displace pathologic bacteria associated with and/or causative of UTI (acute and/or recurring).

The data provided herein demonstrate the safety of intravesicular administration of ASB *E. coli* 2-12 as well as the duration of bladder colonization in healthy beagle dogs and the efficacious microbiologic and clinical effect of intravesicular administration of ASB *E. coli* 2-12 to dogs with naturally-occurring recurrent clinical UTI.

2. Methods of Treating Acute or Recurrent UTI in a Dog a. Dogs Subject to Treatment

The methods find use for alleviating one or more clinical signs (e.g., symptoms) associated with urinary tract infection in a dog. Any dog that has a urine culture that tests positive for a urinary tract infection (e.g., test positive in an aerobic urine culture, e.g., obtained via cystocentesis) can benefit from the present methods. Dogs can benefit from the present methods independent of breed or bloodline. In some embodiments, the dog is a domesticated dog. Dogs of all ages can be affected, but vulnerability increases with advancing age. Additionally, female dogs are more susceptible to bacterial infections of the lower urinary tract than males.

Some dogs with bacterial infections of the lower urinary tract may by asymptomatic, but many dogs will exhibit one or more clinical signs. A few of the more common clinical signs include without limitation:

Difficulty urinating

Blood in urine (hematuria)

Cloudy or malodorous urine

Frequent urination, but only in small amounts

Urinary incontinence, especially during confinement or at places that are not customary (e.g., locations she/he has not peed before)

Urination when bladder is touched (occasional).

In some embodiments, the dog is, in whole or in part, from a hound group breed, a terrier group breed, a herding group breed, a sporting group breed, a working group breed, or a toy group breed, as defined by the American Kennel Club (AKC). Dog breed groups are listed at http://www.akc.org/dog-breeds/groups/. In some embodiments, the dog is of a mixed breed or a breed not recognized by the AKC.

Illustrative dogs from hound group breeds include without limitation Afghan Hound, American English Coonhound, American Foxhound, Basenji, Basset Hound, Beagle, Black and Tan Coonhound, Bloodhound, Bluetick Coonhound, Borzoi, Cirneco dell'Etna, Dachshund, English Foxhound, Greyhound, Harrier, Ibizan Hound, Irish Wolfhound, Norwegian Elkhound, Otterhound, Petit Basset Griffon Vendeen, Pharaoh Hound, Plott, Portuguese Podengo Pequeno, Redbone Coonhound, Rhodesian Ridgeback, Saluki, Scottish Deerhound, Sloughi, Treeing Walker Coonhound and Whippet.

Illustrative dogs from herding group breeds include without limitation Australian Cattle Dog, Australian Shepherd, Bearded Collie, Beauceron, Belgian Malinois, Belgian Sheepdog, Belgian Tervuren, Bergamasco Sheepdog, Berger Picard, Border Collie, Bouvier des Flandres, Briard, Canaan Dog, Cardigan Welsh Corgi, Collie, Entlebucher Mountain Dog, Entlebucher Mountain Dog, Finnish Lapphund, German Shepherd Dog, Icelandic Sheepdog, Miniature American Shepherd, Norwegian Buhund, Old English Sheepdog, Pembroke Welsh Corgi, Polish Lowland Sheepdog, Puli, Pumi, Pyrenean Shepherd, Shetland Sheepdog, Spanish Water Dog and Swedish Vallhund.

Illustrative dogs from terrier group breeds include without limitation Airedale Terrier, American Hairless Terrier, American Staffordshire Terrier, Australian Terrier, Bedlington Terrier, Border Terrier, Bull Terrier, Cairn Terrier, Cesky Terrier, Dandie Dinmont Terrier, Glen of Imaal Terrier, Irish Terrier, Kerry Blue Terrier, Lakeland Terrier, Manchester Terrier, Miniature Bull Terrier, Miniature Schnauzer, Norfolk Terrier, Norwich Terrier, Parson Russell Terrier, Rat Terrier, Russell Terrier, Scottish Terrier, Sealyham Terrier, Skye Terrier, Smooth Fox Terrier, Soft Coated Wheaten Terrier, Staffordshire Bull Terrier, Welsh Terrier, West Highland White Terrier and Wire Fox Terrier.

Illustrative dogs from sporting group breeds include without limitation American Water Spaniel, Boykin Spaniel, Brittany, Chesapeake Bay Retriever, Clumber Spaniel, Cocker Spaniel, Curly-Coated Retriever, English Cocker Spaniel, English Setter, English Springer Spaniel, Field Spaniel, Flat-Coated Retriever, German Shorthaired Pointer, German Wirehaired Pointer, Golden Retriever, Gordon Setter, Irish Red and White Setter, Irish Setter, Irish Water Spaniel, Labrador Retriever, Lagotto Romagnolo, Nova Scotia Duck Tolling Retriever, Pointer, Spinone Italiano, Sussex Spaniel, Vizsla, Weimaraner, Welsh Springer Spaniel, Wirehaired Pointing Griffon and Wirehaired Vizsla.

Illustrative dogs from working group breeds include without limitation Akita, Alaskan Malamute, Anatolian Shepherd Dog, Bernese Mountain Dog, Black Russian Terrier, Boerboel, Boxer, Bullmastiff, Cane Corso, Chinook, Doberman Pinscher, Dogue de Bordeaux, German Pinscher, Giant Schnauzer, Great Dane, Great Pyrenees, Greater Swiss Mountain Dog, Komondor, Kuvasz, Leonberger, Mastiff, Neapolitan Mastiff, Newfoundland, Portuguese Water Dog, Rottweiler, Samoyed, Siberian Husky, Standard Schnauzer, Tibetan Mastiff and St. Bernard.

Illustrative dogs from toy group breeds include without limitation consisting of Affenpinscher, Brussels Griffon, Cavalier King Charles Spaniel, Chihuahua, Chinese Crested, English Toy Spaniel, Havanese, Italian Greyhound, Japanese Chin, Maltese, Manchester Terrier, Miniature Pinscher, Papillon, Pekingese, Pomeranian, Poodle, Pug, Shih Tzu, Silky Terrier, Toy Fox Terrier and Yorkshire Terrier.

b. Intravesicular Instillation of ASB *E. coli* 2-12 Colony Forming Units (CFUs)

The methods entail administering via one or more intravesicular instillations to the bladder of the dog a sufficient number of Asymptomatic Bacteriuria (ASB) *Escherichia coli* 2-12. ASB *E. coli* 2-12 was deposited with American Type Culture Collection (ATCC), 10801 University Boulevard, Manassas, Va. 20110 USA on May 9, 2017 and assigned ATCC Accession No. PTA-124177. In some embodiments, the number of ASB *E. coli* 2-12 bacterial cells instilled into the dog bladder are sufficient to transiently colonize the bladder and to facilitate the reduction, clearing or resolution of the bacteria causing the urinary tract infection. In some embodiments, a range of about $10^6$ to about $10^{11}$ colony forming units (CFUs), a range of about $10^{10}$ to about $10^{11}$ CFUs, e.g., about $10^6$, $10^7$, $10^8$, $10^9$, $10^{10}$, $10^{11}$, $10^{12}$, $10^{13}$, $10^{14}$, $10^{15}$, $10^{16}$ CFUs of ASB *E. coli* 2-12 in a volume of about 5 mL to about 15 mL, e.g., a volume of about 5, 6, 7, 8, 9, 10, 11, 12, 13, 14 or 15 mL, isotonic solution (e.g., sterile saline) are instilled into the dog's bladder, depending on the size of the dog and severity of infection. As appropriate, the ASB *E. coli* 2-12 can be freshly prepared from culture, and can be thawed from lyophilized preparations. The dog can be sedated as necessary for the procedure. Intravesicular instillation procedures into the bladder of a dog are known in the art and commonly placed for various urinary procedures using standard aseptic technique. See, e.g., Torres, et al., *J Am Vet Med Assoc.* 2014 Oct. 1; 245(7):809-11 and Lopez, et al., *J Am Anim Hosp Assoc.* (2014) 50(6):414-6. In some embodiments, in the present methods, the intravesicular instillation procedure does not utilize an indwelling catheter. In some embodiments, in the present methods, the intravesicular instillation procedure utilizes an indwelling catheter. The procedure can be performed in a matter of hours (or <1 hour in many cases), and the dog can return home shortly after the procedure, e.g., after recovering from the sedation.

As needed, the ASB *E. coli* 2-12 can be instilled into the bladder of the dog multiple times, e.g., 2, 3, 4, 5, 6, 7, 8, 9, 10 times, at predetermined intervals or as needed, should the dog's urine test positive for UTI-causing bacteria. In some embodiments, a sufficient number of the ASB *E. coli* 2-12 can be instilled into the bladder of the dog upon a positive determination of pathogenic bacteria in the dog's urine. In some embodiments, a sufficient number of ASB *E. coli* 2-12 are instilled into the bladder of the dog at predetermined intervals, e.g., at regular or irregular intervals of about 2-14 days, e.g., 2-7 days, e.g., about 2, 3, 4, 5, 6, 7, 8, or more, days.

In some embodiments, the methods clear or resolve an acute urinary tract infection in a dog. In some embodiments, the methods delay or eliminate recurring urinary tract infections in a dog. A microbiological cure is achieved when a negative aerobic urine culture obtained via cystocentesis at the designated time point. A clinical cure is achieved when no clinical signs appreciated by the owner of the pet at the designated time point.

3. Monitoring Efficacy

Clinical efficacy can be monitored using any method known in the art. Measurable parameters to monitor efficacy include, but are not limited to, inspection of urine (e.g., for the presence of pathogenic bacteria, blood, and/or foul smell) and behavioral changes in the subject (e.g., difficulty or ease of urination, exhibition of pain when voiding urine, frequency of urination, urinary incontinence, licking of penis/vulvar area). These parameters can be measured using any methods known in the art. As appropriate, the different parameters can be assigned a score. Input can be provided by the client/caretaker/owner of the mammal and/or by self-reporting (in cases where the subject is a human) and/or by a trained clinician.

Observation of the stabilization, improvement and/or reversal of one or more clinical signs (e.g., symptoms) or parameters by a measurable amount indicates that the treatment or prevention regimen is efficacious. Observation of the progression, increase or exacerbation of one or more clinical signs (e.g., symptoms) indicates that the treatment or prevention regimen is not efficacious. For example, observation of reduction or elimination of pathogenic bacteria, blood or foul smell in urine, and/or behavioral changes in the subject (e.g., reduction or elimination of one or more clinical signs (e.g., symptoms) of painful urination, frequent urination of small volumes, urinary incontinence, licking of penis/vulvar area) after one or more bladder instillations of ASB *E. coli* 2-12 indicates that the treatment or prevention regimen is efficacious. Likewise, observation of increased pathogenic bacteria, blood or foul smell in urine, and/or behavioral changes in the subject (e.g., increase or continuance of one or more clinical signs (e.g., symptoms) of painful urination, frequent urination of small volumes, urinary incontinence, licking of penis/vulvar area) after one or more bladder instillations of ASB *E. coli* 2-12 indicates that the treatment or prevention regimen was not efficacious.

As appropriate, efficacy can be monitored over 1, 2, 3, 4, 5, 6, 7, 8, 9, 10, 11, 12, 13, 14, 15, 16, 17, 18, 19, 20, 21, 22, 23, 24 months, or longer, e.g., 1, 1.5, 2, 2.5, 3, 3.5 or 4 years, or longer. In varying embodiments, efficacy may be observed after 1, 2, 3, 4, 5, 6, 7, 8, 9, 10, 11, 12, 13, 14, 15, 16, 17, 18, 19, 20, 21, 22, 23 or 24 months of treatment, with one or more bladder instillations of ASB *E. coli* 2-12.

In certain embodiments, the monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. In certain embodiments, the individuals in the control population have not received prior treatment and do not have an UTI, nor are at risk of developing an UTI. In such cases, if the value of the measurable biomarker or clinical parameter approaches the control value, then treatment is considered efficacious. In other embodiments, the individuals in the control population have not received prior treatment and have been diagnosed with an UTI. In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of clinical signs (e.g., symptoms) of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (i.e., more than a standard deviation) is an indicator that treatment should be resumed in the subject.

4. Kits

Also provided by the present disclosure are kits. In some embodiments, provided are kits that include a composition that includes any of the asymptomatic bacteriuria (ASB) *E. coli* 2-12 described in the Methods and Examples sections of the present disclosure, which sections are incorporated but not reiterated herein for purposes of brevity. Such kits may include a quantity of the ASB *E. coli* 2-12 (e.g., a therapeutic number of colony forming units (CFUs)), present in unit dosages, e.g., ampoules, or a multi-dosage format. As such, in certain embodiments, the kits may include one or more (e.g., two or more) unit dosages (e.g., ampoules) of the composition including ASB *E. coli* 2-12. In some embodiments, a kit of the present disclosure may include about $10^6$-$10^{16}$ colony-forming units (CFU) of ASB *E. coli* 2-12.

As used herein, the term "unit dosage" refers to physically discrete units suitable as unitary dosages for human and animal subjects, each unit containing a predetermined quantity of the composition calculated in an amount sufficient to produce the desired effect. The amount of the unit dosage depends on various factors, such as the particular ASB *E. coli* 2-12 preparation employed, the effect to be achieved, and the pharmacodynamics associated with the ASB *E. coli* 2-12, in the individual. In yet other embodiments, the kits may include a single multi dosage amount of the ASB *E. coli* 2-12 composition.

In some embodiments, a kit of the present disclosure further includes a catheter, e.g., a urethral catheter.

Components of the kits may be present in separate containers, or multiple components may be present in a single container. A suitable container includes a single tube (e.g., vial), or the like.

In some embodiments, a kit of the present disclosure further includes instructions. For example, a subject kit may include instructions for administering the ASB *E. coli* 2-12 composition via one or more intravesicular instillations into the bladder of a dog. In some embodiments, the dog exhibits clinical signs of a UTI, e.g., acute or recurring UTI. The instructions of the kits may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging), etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

EXAMPLES

The following examples are offered to illustrate, but not to limit the claimed invention.

Example 1

Evaluation of the Live Biotherapeutic Product, Asymptomatic Bacteriuria (ASB) *Escherichia coli* 2-12, in Healthy Dogs and Dogs with Clinical Recurrent UTI Summary Background—Antimicrobial resistance is an emerging problem.

Objective—To investigate the safety and efficacy of a live biotherapeutic product, ASB *E. coli* 2-12 for urinary tract infection (UTI) therapy.

Animals—Six healthy research dogs; nine client-owned dogs with recurrent UTI.

Methods—Prospective non-controlled clinical trial. For safety data, research dogs were sedated, a urinary catheter was inserted into the bladder; $10^{10}$ CFU/mL of ASB *E. coli* 2-12 was instilled. Urine was cultured on days 1, 3, and 8-post instillation and dogs were observed for lower urinary tract signs (LUTS). For client owned dogs, ASB *E. coli* 2-12 was instilled similarly and urine cultures analyzed on days 1, 7 and 14 days post instillation.

Results—No LUTS were noted in any of the six research dogs after ASB *E. coli* 2-12 infusion. Pulse field gel electrophoresis (PFGE) studies confirmed the bacterial strains isolated matched that ASB *E. coli* 2-12 strain. Four of the nine client-owned dogs had complete or nearly complete clinical cures by day 14. Of these four dogs, 3 also had microbiological cures at day 14; one of these dogs had subclinical bacteriuria (in addition to ASB *E. coli* 2-12). Three of these four dogs had ASB *E. coli* 2-12 isolated from their urine at day 14. With the exception of mild, temporary, self-limiting, hyporexia in two dogs on the day of biotherapeutic administration, there were no major adverse effects.

Conclusions and clinical importance—These results suggest ASB *E. coli* 2-12 is safe and efficacious for treating clinical UTI in dogs.

Methods

ASB *E. coli* 2-12 Preparation. ASB *E. coli* 2-12 is a clinical isolate of *E. coli* obtained from the urine of a patient with asymptomatic bacteriuria (11,14). ASB *E. coli* 2-12 was deposited with American Type Culture Collection (ATCC), 10801 University Boulevard, Manassas, Va. 20110 USA on May 9, 2017 and assigned ATCC Accession No. PTA-124177. ASB *E. coli* 2-12 was cultured through serial passages at 37° C. in Luria broth supplemented with 50 mg/mL streptomycin and 100 mg/mL ampicillin under the following conditions: shaking at 225 rpm for 16-18 hours, subsequently diluted 1:1000 into fresh broth, cultured under static conditions for 24 hours, and followed by an additional dilution into fresh medium and culture for another 24 hours under static conditions. Bacterial cultures were centrifuged at 6000 rpm for 20 minutes at 4° C. Pelleted bacteria were washed with ice-cold Dulbecco's PBS and centrifuged again as above. Bacteria were quantified at OD420 nm and then recovered by centrifugation as above. The bacterial cell pellet was resuspended in sterile, ice-cold inulin preservation solution (4.5% inulin (Alfa Aesar) and 1.0% glycerol in ddH2O) to achieve a final concentration of $2 \times 10^{10}$ CFU/ml, and 1 mL single-dose aliquots were transferred to sterile cryovials. Lyophilization was carried out at room temp for 18-24 hrs, and vials were then stored at −80° C. Following reconstitution in sterile PBS, preserved-and-stored ASB *E. coli* 2-12 aliquots retained approximately 69% of viability.

Safety Studies: In this prospective, non-controlled clinical safety trial, six female intact 3-year old purpose-bred beagle dogs were utilized for the first part of the study. All dogs were deemed healthy based on a normal physical examination and the absence of abnormalities on a CBC, serum biochemical panel, and urinalysis. All dogs had a negative baseline aerobic bacterial urine culture before entering the study and were housed at the University of California-Davis Animal Care Facilities.

On day 0, dogs received 10 μg/kg dexmedetomidine and 0.3 mg/kg of butorphanol IM to provide chemical restraint. Once appropriate sedation was achieved, the vulvar area was clipped to remove excess hair and cleaned with chlorhexidine solution. A 6 Fr cathetera was inserted into the urinary bladder using aseptic technique. All urine was removed from the bladder. A total of $10^{10}$ colony-forming units (CFU) of ASB *E. coli* 2-12 (reconstituted in 10 mL of sterile saline from lyophilized bacteria) was instilled into the bladder. This bacterial strain is highly sensitive to the most commonly used antimicrobials but is characterized by resistance to ampicillin and ticarcillin. The catheters were left in place for approximately 1 hour while the dogs recovered from sedation. Dogs were monitored daily for changes in appetite and lower urinary tract signs (LUTS) including stranguria, hematuria and pollakiuria.

Urine specimens (5 mL) were collected by antepubic cystocentesis on days 1 and 3, and by urinary catheterization on day 8. After collecting urine on day 8, instillation of bacteria was repeated as described above and urine collected by cystocentesis on days 9, 11 and 16. All urine specimens were submitted to the University of California-Davis Veterinary Medical Teaching Hospital (VMTH) microbiology laboratory for routine urinalysis and aerobic bacterial urine culture by inoculation of 10 μL of urine on to 5% defibrinated sheep blood and MacConkey agars incubated at 35° C. in room air with added 5% CO2. Susceptibility testing using the Clinical Laboratory Standards Institute methodology was performed (15). If protein was detected on urinalysis, the urine protein/creatinine ratio was determined. A final urine culture was also performed on day 30. Bacterial strain typing was performed using pulsed field gel electrophoresis (PFGE) as previously described (16). This portion of the study was approved by the Institutional Animal Care and Use Committee at the University of California-Davis (protocol #17782). All animals were adopted after study completion.

Clinical efficacy study. This was also a non-placebo controlled, prospective clinical pilot trial. At least 9 patients with the same histology or molecular target need to be treated with the investigational drug to test the null hypothesis of insufficient efficacy therefore, this was considered a phase II pilot study (17). Assuming the likelihood of spontaneous regression of UTI is less than 5% and expecting at least a 25% response rate for the ASB *E. coli* 2-12 treated dogs to be clinically useful, with a P=0.05 (type I [a] error; false positive) and a power of 0.8 (type II [b] error; false negative), then 9 dogs would be needed in this pilot study.

Dogs with a history of three or more recurrent clinical UTIs over a one-year time period where no underlying predisposing factors were documented, except those limited to voiding disorders, were eligible for enrollment. Dogs were enrolled at two study sites, the University of California-Davis VMTH in Davis, Calif., USA and the Koret School of Veterinary Medicine, Hebrew University of Jerusalem, Israel. Exclusion criteria included dogs with underlying comorbidities that could predispose to UTI including cystic neoplasia, cystic and/or renal calculi, moderate or severe polypoid cystitis, ectopic ureters and other urogenital congenital abnormalities, as well as systemic disorders such as systemic neoplasia, diabetes mellitus and hyperadrenocorticism. Dogs were also excluded if antimicrobials had been administered within the 3 days prior to enrollment, or if glucocorticoids had been administered within 2 weeks prior to enrollment. Only standard ectoparasite and endoparasite preventative medication was allowed to be administered during the study period. If dogs had received the long-duration cephalosporin cefovecin,[b] they were also deemed ineligible, due to the variable half-life of that antibiotic and duration of its effect.

All dogs had a complete blood count, serum biochemical panel, urinalysis and abdominal ultrasound performed prior to ASB *E. coli* 2-12 installation to ensure there was no evidence of any of the exclusion criteria. If pyuria and bacteriuria were noted on the urinalysis, the urine was submitted for culture and the dog was sedated with 2.5-10 μg/kg of dexmedetomidine (sufficient for urinary catheterization), and the ASB *E. coli* 2-12 was infused as described for the healthy dogs.

The sedation was not reversed and the catheter was removed approximately 30 minutes after the ASB *E. coli* 2-12 was instilled. Only dogs with positive urine cultures were finally enrolled. The dogs were evaluated again at their respective institutions on days 1, 7 and 14 post ASB *E. coli* 2-12 infusion and a urine specimen was collected by ultrasound guided cystocentesis for urinalysis and aerobic bacterial urine culture.

Any *E. coli* isolates from these clinical dogs were stored at −80° C. from each dog on each visit, and PFGE was performed, according to a protocol developed by the Centers for Disease Control and Prevention (CDC) for *Salmonella*, *Escherichia coli* O157:H7, non-*Escherichia coli* O157:H7, and *Shigella* using *Salmonella enterica* serotype Braenderup H9812 as the control strain (18).

Owners were also asked to complete a daily questionnaire regarding their dog's lower urinary tract voiding habits during the two-week study period. Owners were asked to rank on a 0-3 scale the presence and frequency of pollakiuria, hematuria, stranguria, licking of the penis/vulvar area, and the presence or absence of urinary incontinence. This portion of the study was approved by Institutional Animal Care and Use Committee at the University of California-Davis (protocol #18658) and the Koret School of Veterinary Medicine, The Hebrew University, Jerusalem, Israel (protocol #KSVM_VTH/04-2015).

Results

Safety Studies: All baseline CBC, biochemical panel and urinalysis findings in the purpose-bred Beagle dogs were within reference ranges. No complications were encountered during instillation of the ASB *E. coli* 2-12. Lower urinary tract signs were not detected in any of the dogs during the study period.

Urine culture and relevant urinary sediment results are shown in Tables 1 and 2. ASB *E. coli* 2-12 was present in the urine of 4/6 dogs 1 day post-instillation, 1/6 dogs 3 days post-instillation and none of the dogs 8 days post-instillation, as determined by urine culture and pulsed-field gel electrophoresis (PFGE). One dog (dog 5) had a low magnitude ($3\times10^2$ CFU/mL) growth of *Streptococcus* colonies, 8 days post-instillation, but had a negative urine culture on day 9. No dogs had pyuria on urine sediment examination.

TABLE 1

Urinalysis and aerobic urine culture results from six healthy beagle dogs after first instillation of ASB *E. coli* 2-12 into the urinary bladder

|  | Aerobic Urine Culture | | | CFU/mL | | | WBC/HPF | | | RBC/HPF | | |
|---|---|---|---|---|---|---|---|---|---|---|---|---|
|  | Day 1 | Day 3 | Day 8 | Day 1 | Day 3 | Day 8 | Day 1 | Day 3 | Day 8 | Day 1 | Day 3 | Day 8 |
| Dog 1 | *E. coli* | NG | NG | $1.8 \times 10^3$ | — | — | 0-3 | 0-3 | 0-3 | >100 | 0 | 0-3 |
| Dog 2 | NG | NG | NG | — | — | — | 0-3 | 0-3 | 0-3 | >100 | 0-2 | 0 |
| Dog 3 | *E. coli* | *E. coli* | NG | $2.0 \times 10^2$ | $1 \times 10^5$ | — | 0-3 | 0-3 | 0-3 | >100 | 3-5 | 0-3 |
| Dog 4 | *E. coli* | NG | NG | $2.7 \times 10^3$ | — | — | 0-3 | 0-3 | 0-3 | >100 | 0-1 | 0 |
| Dog 5 | *E. coli* | NG | Streptococcus spp. | $1.2 \times 10^4$ | — | $3 \times 10^2$ | 0-3 | 0-3 | 0-3 | >100 | 0 | 0-3 |
| Dog 6 | NG | NG | NG | — | — | — | 0-3 | 0-3 | 0-3 | 8-12 | 0 | 0-2 |

CFU/mL = colony forming units/milliliter;
WBC/HPF = white blood cells per high power field;
RBC/HPF = red blood cells per high power field;
NG = no growth

TABLE 2

Urinalysis and aerobic bacterial urine culture results from six healthy beagle dogs after a second instillation of ASB *E. coli* 2-12 into the urinary bladder 8 days after the first treatment.

| | Aerobic Urine Culture | | | CFU/mL | | | WBC/HPF | | | RBC/HPF | | |
|---|---|---|---|---|---|---|---|---|---|---|---|---|
| | Day 9 | Day 11 | Day 16 | Day 9 | Day 11 | Day 16 | Day 9 | Day 11 | Day 16 | Day 9 | Day 11 | Day 16 |
| Dog 1 | *E. coli* | NG | NG | $1.2 \times 10^2$ | — | — | 0-3 | 0-3 | 0-3 | 18-24 | >100 | 25-50 |
| Dog 2 | NG | NG | NG | — | — | — | 0-3 | 0-3 | 0-3 | 8-12 | 8-12 | 0-3 |
| Dog 3 | NG | NG | NG | — | — | — | 0-3 | 0-3 | 0-3 | 0-3 | 0-3 | 0-1 |
| Dog 4 | *E. coli* | NG | NG | $1.2 \times 10^3$ | — | — | 0-3 | 0-3 | 0-3 | 50-100 | 0-3 | 0-3 |
| Dog 5 | NG | NG | NG | — | — | — | 0-3 | 0-3 | 0-3 | 0-1 | 0-3 | 0-1 |
| Dog 6 | NG | NG | NG | — | — | — | 0-3 | 0-3 | 0-3 | 6-8 | >100 | 0-2 |

CFU/mL = colony forming units/milliliter;
WBC/HPF = white blood cells per high power field;
RBC/HPF—red blood cells per high power field;
NG = no growth One day after the second instillation of ASB *E. coli* 2-12 (day 9), one dog had minimal growth ($1 \times 10^5$ CFU/mL) of ASB *E. coli* 2-12 and all subsequent cultures were negative. Pyuria was again not detectable in any of the dogs. On day 30, culture of the urine from one dog yielded $3 \times 10^2$ CFU/mL of a non-enteric bacterial species as well as *Mycoplasma* spp. No LUTS were noted in that dog and a follow-up culture was not obtained. The UPC was consistently ≤0.2 (within reference range), when proteinuria was detected on dipstick examination from all urine specimens.

Figure 1:
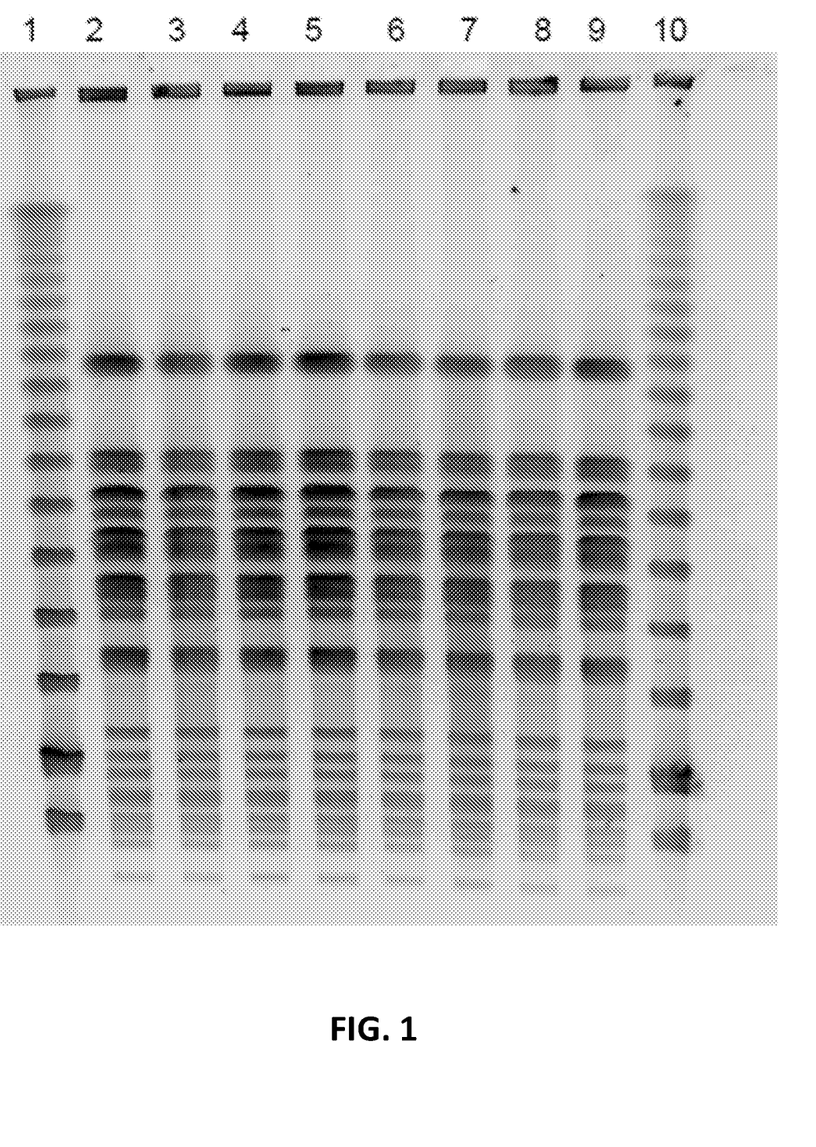
FIG. 1 illustrates pulse field gel electrophoresis profiles from urine *E. coli* isolated from research dogs. Lane 2 is ASB *E. coli* 2-12 (lane 2) control from the lyophilized sample. Lanes 3-9 represent the seven *E. coli* isolates obtained from the research dogs after inoculation. The *E. coli* isolates were genetically identical. Low range PFGE biomarkers are represented in lanes 1 and 10.

The *E. coli* strains isolated had the same susceptibility profile and were consistently resistant to ampicillin and ticarcillin. Furthermore, PFGE analysis confirmed that the PFGE type of all *E. coli* strains isolated matched that of the ASB *E. coli* 2-12 strain (FIG. 1).

Clinical Efficacy of ASB 2-12: Nine dogs were recruited for this aim of the study; five from the University of California-Davis and four from The Koret School of Veterinary Medicine. Four dogs were mixed breeds and one of each of the following: Golden retriever, Anatolian shepherd, German shorthaired pointer, German shepherd and a dachshund. Median weight was 21 kg (range 7.6-29.6 kg). Seven were female (6 spayed and 1 intact); and 2 were castrated males; the median age was 8 years (range 0.5-13 years). One dog had clinical signs of pollakiuria only, and four dogs had pollakiuria, hematuria and stranguria. These dogs had no other comorbidities. One dog, dog 3, had its right thoracic limb amputated 3 years before enrollment. This dog had stranguria, pollakiuria and hematuria. Dog 4 had a T3-L3 myelopathy and was evaluated for pronounced urinary incontinence and mild hematuria that responded to antimicrobial treatment associated with its UTI. Dog 7 had a right pelvic limb amputated 6 years before enrollment due to an osteosarcoma. This dog had mild osteoarthritis and weakness in his left pelvic limb and was evaluated for stranguria and pollakiuria. Dog 8 was a dachshund that had intervertebral disc disease, required a cart for mobility, and assistance with micturition using manual bladder expression. This dog developed hematuria and pronounced urinary incontinence that were associated with UTI and these signs were reported to have resolved with proper antimicrobial treatment. With the exception of mild normocytic normochromic nonnegative anemia (HCT 36%, reference range, 40-55% in one dog (dog 9), none of the other eight dogs had abnormalities on CBC and serum chemistry prior to enrollment.

Urinalysis and Microbiologic outcomes. All 9 dogs screened had positive urine culture and were formally enrolled in the study (Table 3). Three dogs (dogs 7, 8 and 9) showed persistently positive culture results and in the remaining 6 dogs the infecting pathogen was not isolated by day 14. Of the latter 6 dogs, 3 (dogs 1, 2, and 3) also had MC at day 14 and a fourth dog (dog 4) had MC at days 1 and 7 followed by subclinical reinfection (in addition to ASB *E. coli* 2-12) at day 14 and antimicrobials were not clinically indicated. Three of the four dogs with MC had ASB *E. coli* 2-12 isolated from their urine on day 14 documented by PFGE. Two dogs (dogs 5 and 6) had MC documented with only ASB *E. coli* 2-12 growth on day 1, but by day 7, clinical signs and reinfections with new strains of bacteria were documented. In the remaining dog (dog 9), ASB *E. coli* 2-12 was never isolated.

TABLE 3

Urine culture outcomes in 9 dogs with naturally-occurring recurrent clinical bacterial cystitis.

| | Day 0 | Day 1 | Day 7 | Day 14 | Summary Outcome |
|---|---|---|---|---|---|
| Dog 1 | *Proteus* spp | *Proteus* spp | *Entero-coccus* spp | NG | CC, MC |
| Dog 2 | *Staph* spp | *E. coli* spp* | *E. coli* spp* | *E. coli* spp* | CC, MC |
| Dog 3 | *E. coli* spp | *E. coli* spp* | *E. coli* spp* | *E. coli* spp* | CC, MC |
| Dog 4 | *E. coli* spp 2 strains | *E. coli* spp* 3 strains | *E. coli* spp* 3 strains | 2 *Entero-coccus* spp 2 *E. coli* spp* | CC Non-clinical reinfection |
| Dog 5 | *Proteus* spp | *E. coli* spp* | *Proteus* spp | NG, on antibiotics | MC, reinfection |
| Dog 6 | *Proteus* spp | *E. coli* spp* | *E. coli* spp | *Proteus* spp | MC, reinfection |
| Dog 7 | *E. coli* spp. | Developed emphysematous cystitis | Clinical Failure | NA | CF, MF |

TABLE 3-continued

Urine culture outcomes in 9 dogs with naturally-occurring recurrent clinical bacterial cystitis.

| | Day 0 | Day 1 | Day 7 | Day 14 | Summary Outcome |
|---|---|---|---|---|---|
| Dog 8 | *Proteus* spp & *Staph.* spp | *Proteus, E. coli\*, Staph* spp | *Proteus, E. coli\*, Staph* spp | NG, on antibiotics | CF MF |
| Dog 9 | *E. coli* spp. | *E. coli* spp. | *E. coli* spp. | *E. coli* spp 2 strains. | CF MF |

*E. coli* isolate is ASB *E. coli* 2-12 as identified by pulse field gel electrophoresis.
MC = Microbiological Cure.
CC = Clinical Cure,
MF = Microbiological Failure,
CF = Clinical Failure.
NG = No growth.
NA = Not applicable.

Of the three dogs considered microbiologic failures, ASB *E. coli* 2-12 was isolated from one dog on days 1 and 7, but both the original pathogen and clinical signs persisted. In one dog, emphysematous cystitis was documented 24-hours post ASB *E. coli* 2-12 inoculation and this dog was deemed a clinical failure. All clinical signs and evidence of emphysematous cystitis resolved after initiation of antimicrobial therapy. One dog showed no colonization with ASB *E. coli* 2-12 and no eradication of the initial infecting pathogen.

Long-term follow up urine cultures were only available in dogs 5 and 6. ASB *E. coli* 2-12 (as determined by PFGE analysis) was isolated 60 days after bacterial instillation and these two dogs remained free of LUTS for more than 6 months.

Figure 2:
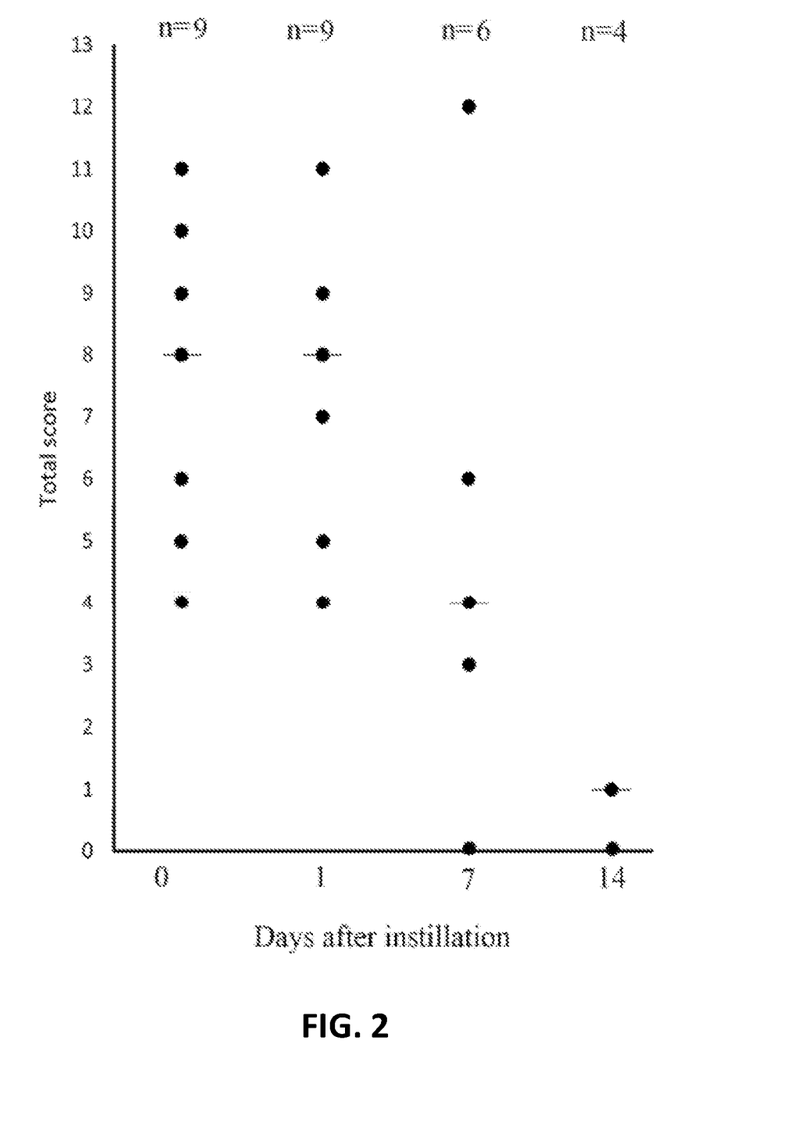
FIG. 2 illustrates scatter plot of voiding diary scores of the dogs that had clinical improvements noted. Dash line indicates the median.

Clinical outcomes. Four dogs had complete or nearly complete clinical cures by day 14 based on voiding diary scores (FIG. 2). Three of these dogs also had microbiologic cures. Of the dogs that had clinical improvements, the median total LUTS score on day 0 was 8 (range, 5-11). On days 1, 7 and 14 after ASB *E. coli* 2-12 instillation median scores were 8 (range, 4-11), 4 (range, 0-12) and 1 (range, 0-2), respectively (FIG. 2). Although ASB *E. coli* 2-12 was never isolated from Dog 2, a clinical cure was documented for 11 months.

Adverse effects. The only clinical adverse effects reported post instillation of ASB *E. coli* 2-12 were in two dogs in which the owners described a mild, self-limiting decrease in appetite at the day of the procedure, which resolved in both dogs within 24 hours. Ultrasonographic evidence of emphysematous cystitis was also noted in one dog.

Discussion

We have documented a clinically applicable, easy and safe method to administer the live biotherapeutic product (LBP) ASB *E. coli* 2-12, to dogs. By evaluating the ASB *E. coli* 2-12 strain in healthy dogs first, we were able to develop a protocol that translated well into the clinical setting (procedure time <20 minutes). The isolated *Streptococcus* spp. from the urine of one research dog just prior to the second instillation of ASB *E. coli* 2-12, might have been a contaminant from urine collection by catheterization on day 8. ASB *E. coli* 2-12 was isolated from the dogs after inoculation, however bacterial colonization was short-lived. These findings are similar to a previously published study where ASB *E. coli* was cleared from the urine of healthy mice within days after instillation (11). Similar findings were reported in dogs treated with ASB *E. coli* 83972 (13,19). However, that dog study evaluated a multi-dose regimen (13) requiring an indwelling urinary catheter throughout the study period, which allowed multiple administrations of the ASB *E. coli* 83972 strain. This might have been one reason a single dog had colonization of the bacteria for 28 days. We chose to design a protocol that would allow easier translation to the clinical setting and would not place dogs at high risk for iatrogenic bacterial infection due to prolonged urinary catheterization, so indwelling catheters were not utilized.

After a single instillation of ASB *E. coli* 2-12 into the bladders of 9 dogs with clinical recurrent UTI, five dogs had a MC of the initial bacterial infection on day 14, although two had documented reinfections with a new bacterial strain. Clinical cures were documented in four cases on day 14. PFGE confirmed at least transient colonization with ASB *E. coli* 2-12 in 6 dogs (range 1-60 days). We also noted a lack of recurrent infections in three dogs, which is intriguing. These results were achieved in both the presence (dogs 2 and 3) and absence (dog 1) of ASB *E. coli* 2-12. The combination of these acute microbiologic and clinical effects coupled with some durable prophylactic benefits suggests that ASB *E. coli* 2-12 has potential antimicrobial, and analgesic activity which was noted in the murine studies (11).

Of several ASB strains that have been investigated for treatment of recurrent UTIs, ASB *E. coli* 2-12 has shown the greatest analgesic activity in mouse models when compared to *E. coli* 83972, which is why we selected this strain for our studies (11). Intravesicular or intravaginal administration of ASB *E. coli* 2-12 in a NU14 *E. coli*-induced cystitis mouse model led to a rapid and significant decrease in UTI-associated allodynia. Furthermore, ASB *E. coli* 2-12 exhibited superior analgesic activity compared to ciprofloxacin for UTI induced by non-UPEC bacteria (e.g. *Proteus mirabilis* and *Klebsiella pneumoniae*) in mouse studies. Without being bound to theory, it is also possible that ASB *E. coli* 2-12 might exert an immunostimulatory, adjuvant-like activity that promotes an effective host immune response sufficient to clear uropathogens after ASB clearance, as has been recently shown for BCG-mediated clearance of *E. coli* in human patients (20). Clinical efficacy of ASB *E. coli* 2-12 in dog UTI can result from a combination of immunomodulation that promotes microbiologic relief and analgesic activity that provides symptomatic relief.

No major adverse events were reported. However, one dog had ultrasonographic evidence of emphysematous cystitis. It is unknown if the original bacteria, or the instillation of ASB *E. coli* 2-12 were the cause of this observation and the dog's signs resolved quickly with antimicrobial administration. Two dogs experienced hyporexia that resolved within 24 hours after the infusion of the ASB *E. coli* 2-12, which might have been the result of residual effects of the sedatives, as seen commonly in veterinary practice after other procedures involving sedation. In some of the dogs with naturally-occurring bacterial cystitis, the duration of ASB *E. coli* 2-12 colonization was longer when compared to the healthy female beagles. It is possible that dogs with recurrent lower UTI have compromised local defense mechanisms that are less effective at clearing bacterial infections, which enables more prolonged colonization by the ASB *E. coli* 2-12 strain compared to healthy dogs (21).

While some dogs were considered clinical failures, one should consider that dogs in our study had complicated UTI. Although we excluded cases with immunosuppressive disorders and overt nidus for infection that was documented, we enrolled dogs with micturition abnormalities, as long as the historical clinical signs associated with the UTI responded to antimicrobial therapy. For example, three dogs had incomplete micturition due to orthopedic or neurological problems. Two of these dogs relapsed with clinical signs early in the course of treatment; one developed emphysematous cystitis, and the other had intervertebral disk disease. While dog nine also had a T3-L3 myelopathy, this dog's clinical signs waxed and waned during the initial two weeks after the instillation of the ASB *E. coli* 2-12, but further antimicrobial therapy was not clinically indicated for this dog again until approximately six months later. Co-colonization of ASB *E. coli* 2-12 with the other strains of *E. coli* in the bladder were noted.

Alternative approaches for prevention and treatment of recurrent UTI that have been investigated in human beings as well as animal UTI models include the use of cranberry extract (22,23), cranberry juice (24), probiotics (25,26), live biotherapeutic products (LPBs) (10,11), vaccines (27) and various other alternative therapies (28). Live biotherapeutic products appear promising for treatment of recurrent UTI for several reasons. Intravesicular administration of *E. coli* ASB 83972 in human beings with recurrent UTI can reduce symptoms of UTI and protect some patients from recurrent UTI after serial catheterizations (29) which might reduce the need to antimicrobial therapy.

This study had limitations. First, the study was short-term and we only carefully followed dogs during the initial 14 days post ASB *E. coli* 2-12 instillation. However, long-term information on a few of these dogs was available and provided on an individual case basis. Second, this was a pilot study including only 9 dogs. A larger number of dogs with a control group are needed to establish clinical efficacy of this treatment modality, as some apparent responses might have resulted from immune clearance or waxing and waning of clinical signs over time. This was a pilot study so no control group was evaluated. Bacterial cystitis can resolve spontaneously in some patients, therefore we must consider that some dogs might have responded with or without the ASB *E. coli* 2-12 instillation. Prospective controlled clinical trials are warranted. Finally, we only investigated one dosing regimen. Studies evaluating *E. coli* 83972 for clinical recurrent UTI in humans with spinal cord injury were inoculated post antimicrobial treatment 3 times daily for three days. Preliminary findings suggested the colonization decreased UTI in these treated patients (9). Therefore, evaluating multiple instillations of ASB *E. coli* 2-12 in clinical dogs could be evaluated to see if improved clinical outcomes are noted.

REFERENCES

1. Ling G V. Therapeutic strategies involving antimicrobial treatment of the dog urinary tract. J Vet Med Assoc 1984; 185:1162-1164.
2. Westropp J L, Sykes J E, from S, et al. Evaluation of the efficacy and safety of high dose short duration enrofloxacin treatment regimen for uncomplicated urinary tract infections in dogs. J Vet Intern Med 2012; 26:506-512.
3. Foxman B Epidemiology of urinary tract infections: incidence, morbidity, and economic costs. Am J Med 2002; 113 Suppl 1A:5S-13S.
4. Seguin M A, Vaden S L, Altier C, et al. Persistent urinary tract infections and reinfections in 100 dogs (1989-1999). J Am Vet Intern Med 2003; 17:622-631.
5. Norris C R, Williams B J, Ling G V, et al. Recurrent and persistent urinary tract infections in dogs: 383 cases (1969-1995). J Am Anim Hos Assoc 2000; 36:484-492.
6. Chang S K, Lo D Y, Wei H W, et al. Antimicrobial resistance of *Escherichia coli* isolates from dog urinary tract infections. J Vet Med Sci 2015; 77:59-65
7. Weese J S. Antimicrobial resistance: time for action. Vet Rec 2011; 169:122-123.
8. Weber G, Riesenberg K, Schlaeffer F, et al. Changing trends in frequency and antimicrobial resistance of urinary pathogens in outpatient clinics and a hospital in Southern Israel, 1991-1995. Eur J Clin Microbiol Infect Dis 1997; 16:834-838.
9. Hull R, Rudy D, Donovan W, et al. Urinary tract infection prophylaxis using *Escherichia coli* 83972 in spinal cord injured patients. J Urol 2000; 163:872-877.
10. Darouiche R O, Thornby J I, Cerra-Stewart C, et al. Bacterial interference for prevention of urinary tract infection: a prospective, randomized, placebo-controlled, double-blind pilot trial. Clin Infect Dis 2005; 41:1531-1534.
11. Rudick C N, Taylor A K, Yaggie R E, et al. Asymptomatic Bacteriuria *Escherichia coli* Are Live Biotheraputics for UTI. PloS one 2014; 9:e109321.
12. Thompson M F, Litster A L, Platell J L, et al. Dog bacterial urinary tract infections: new developments in old pathogens. Vet J 2011; 190:22-27.
13. Thompson M F, Schembri M A, Mills P C, et al. A modified three-dose protocol for colonization of the dog urinary tract with the asymptomatic bacteriuria *Escherichia coli* strain 83972. Vet Micro 2012; 158:446-450.
14. Hultgren S J, Schwan W R, Schaeffer A J, et al. Regulation of production of type 1 pili among urinary tract isolates of *Escherichia coli*. Infect Immun 1986; 54:613-620.
15. 2008 Performance Standards for Antimicrobial Disk and Dilution Susceptibility Test for Bacteria Isolated from Animals; Approved Standard-Third Edition. In: 2008.
16. Kruger E F, Byrne B A, Pesavento P, et al. Relationship between clinical manifestations and pulsed-field gel profiles of *Streptococcus canis* isolates from dogs and cats. Vet Micro 2010; 146:167-171
17. Vail D M. Cancer clinical trials: development and implementation. Vet Clin North Am Small Am Prac 2007; 37:1033-1057; v. Review.
18. Ribot E M, Fair M A, Gautom R, et al. Standardization of pulsed-field gel electrophoresis protocols for the subtyping of *Escherichia coli* O157:H7, *Salmonella*, and *Shigella* for PulseNet. Foodborne Pathog Dis 2006; 3:59-67
19. Thompson M F, Totsika M, Schembri M A, et al. Experimental colonization of the dog urinary tract with the asymptomatic bacteriuria *Escherichia coli* strain 83972. Vet Micro 2011; 147:205-208.
20. Herr H W. Intravesical Bacille Calmette-Guerin Eradicates Bacteriuria in Antibiotic-naive Bladder Cancer Patients. Eur Urol 2013; 63:832-835.
21. Spencer J D, Schwaderer A L, Becknell B, et al. The innate immune response during urinary tract infection and pyelonephritis. Pediatr Nephrol 2014; 29:1139-1149.
22. McMurdo M E, Argo I, Phillips G, et al. Cranberry or trimethoprim for the prevention of recurrent urinary tract infections? A randomized controlled trial in older women. J Antimicrob Chemother 2009; 63:389-395
23. Tempera G, Corsello S, Genovese C, et al. Inhibitory activity of cranberry extract on the bacterial adhesiveness in the urine of women: an ex-vivo study. Int J Immunopathol Pharmacol 2010; 23:611-618.
24. Stapleton A E, Dziura J, Hooton $T_M$, et al. Recurrent urinary tract infection and urinary *Escherichia coli* in women ingesting cranberry juice daily: a randomized controlled trial. May Clin Proc 2012; 87:143-150.

25. Rodrigues F, Maia M J, das Neves J, et al. Vaginal suppositories containing *Lactobacillus acidophilus*: development and characterization. Drug Dev Ind Pharm 2014:1-8.
26. Stapleton A E, Au-Yeung M, Hooton $T_M$, et al. Randomized, placebo-controlled phase 2 trial of a *Lactobacillus crispatus* probiotic given intravaginally for prevention of recurrent urinary tract infection. Clin Infect Dis 2011; 52:1212-1217.
27. Billips B K, Yaggie R E, Cashy J P, et al. A live-attenuated vaccine for the treatment of urinary tract infection by uropathogenic *Escherichia coli*. The J Infect Dis 2009; 200:263-272.
28. Mansour A, Hariri E, Shelh S, et al. Efficient and cost-effective alternative treatment for recurrent urinary tract infections and interstitial cystitis in women: a two-case report. Case Rep Med 2014; 2014:698758.
29. Sunden F, Hakansson L, Ljunggren E, et al. *Escherichia coli* 83972 bacteriuria protects against recurrent lower urinary tract infections in patients with incomplete bladder emptying. J Urol 2010; 184:179-185

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a recurrent clinical urinary tract infection (UTI) in a dog having a history of UTIs, the method comprising administering via one or more intravesicular instillations into the bladder of the dog a sufficient number of asymptomatic bacteriuria (ASB) *E. coli* 2-12 CFUs, wherein ASB *E. coli* 2-12 is deposited with the American Type Culture Collection under Accession Number PTA-124177, and wherein the dog does not experience a recurrent UTI within 2 months of receiving a first instillation of ASB *E. coli* 2-12.

2. The method of claim 1, wherein $10^6$-$10^{16}$ colony-forming units (CFU) of ASB *E. coli* 2-12 are instilled into the bladder.

3. The method of claim 2, wherein $10^{10}$-$10^{11}$ colony-forming units (CFU) of ASB *E. coli* 2-12 are instilled into the bladder.

4. The method of claim 1, wherein an indwelling catheter is not used.

5. The method of claim 1, wherein the dog has one or more clinical signs of pollakiuria, hematuria and/or stranguria at the time of the first instillation of ASB *E. coli* 2-12.

6. The method of claim 1, wherein the dog does not have one or more clinical signs of pollakiuria, hematuria and/or stranguria at the time of the first instillation of ASB *E. coli* 2-12.

7. The method of claim 1, wherein the dog does not have and is not suspected of having cystic neoplasia, cystic calculi, an uncorrected ectopic ureter.

8. The method of claim 1, wherein the dog has not been administered an antibiotic within 3 days prior to the first instillation of ASB *E. coli* 2-12.

9. The method of claim 8, wherein the dog has not received Cefovicin prior to the first instillation of ASB *E. coli* 2-12.

* * * * *